United States Patent [19]

Lesher et al.

[11] Patent Number: 4,506,075

[45] Date of Patent: Mar. 19, 1985

[54] PROCESS OF PREPARING CARDIOTONIC 3-METHYL-4-(4-PYRIDINYL)BENZENEAMINES

[75] Inventors: George Y. Lesher, Schodack; Baldev Singh, East Greenbush, both of N.Y.

[73] Assignee: Sterling Drug Inc., New York, N.Y.

[21] Appl. No.: 485,086

[22] Filed: Apr. 14, 1983

Related U.S. Application Data

[62] Division of Ser. No. 347,086, Feb. 8, 1982, Pat. No. 4,415,578.

[51] Int. Cl.³ .................. C07D 213/73; C07D 213/74
[52] U.S. Cl. .................................................... 546/329
[58] Field of Search ......................................... 546/329

[56] References Cited

FOREIGN PATENT DOCUMENTS 518886 3/1940 United Kingdom .

OTHER PUBLICATIONS

Smith, P. A. S. "Open Chain Nitrogen Compounds", (1965), p. 93.
Koenigs et al., Ann., 509, 142–158, (1934).
Forsythe et al., J. Chem. Soc. 2921, (1926).

Primary Examiner—Henry R. Jiles
Assistant Examiner—Dale A. Bjorkman
Attorney, Agent, or Firm—William G. Webb; B. Woodrow Wyatt; Paul E. Dupont

[57] ABSTRACT

3-Methyl-4-(4-pyridinyl)benzeneamines, useful as cardiotonic agents, are prepared by reaction of pyridine, benzoyl chloride and an appropriate 3-methyl-N,N-di-lower-alkylbenzeneamine in the presence of copper powder and decomposing the reaction mixture with alkali and, if desired, reacting a resulting 3-methyl-4-(4-pyridinyl)N,N-di-lower-alkylbenzeneamine with hydrogen bromide and pyridine to obtain 3-methyl-4-(4-pyridinyl)benzeneamine.

3 Claims, No Drawings

PROCESS OF PREPARING CARDIOTONIC 3-METHYL-4-(4-PYRIDINYL)BENZENEAMINES

RELATED APPLICATIONS

This application is a division of application Ser. No. 347,086, filed Feb. 8, 1982, now U.S. pat. No. 4,415,578, patented Nov. 15, 1983.

BACKGROUND OF THE INVENTION (a) Field of the Invention

This invention relates to 3-methyl-4-(4-pyridinyl)-benzeneamines, which are useful as cardiotonic agents, to cardiotonic compositions containing the same, a method of increasing cardiac contractility using the same and to chemical processes for the preparation thereof.

(b) Description of the Prior Art

Koenigs et al., Ann., 509, 142-158 (1934) disclose, on pages 147-148, the preparation of 4-(4-pyridinyl)-N,N-dimethylbenzeneamine for which no utility is asserted. The compound is prepared by heating on a water bath a mixture of 16 g. (0.202 mole) of pyridine with 14 g. (0.099 mole) of benzoyl chloride in the presence of 0.5 g. (0.0079 mole) of copper powder and then treating the cooled reaction mixture with 12 q. (0.098 mole) of N,N-dimethylbenzeneamine (i.e. N,N-dimethylaniline) followed by heating for five hours on a water bath, the ratio of pyridine to benzoyl chloride to dimethylaniline to copper thus being 2:1:1:0.079. However in a section on pages 150-151 entitled (in translation) "Condensation Products from m-Dimethylamino-toluene, Pyridine and Benzoyl Chloride", the authors describe a similar reaction using the same reaction conditions and precisely the same molar ratios of reactants, except that 3-methyl-N,N-dimethylbenzeneamine (i.e. dimethyl-m-toluidine) was used in place of the N,N-dimethylbenzeneamine used in the procedure described on pages 147-148 of the reference. The product obtained is identified only by its empirical formula, which corresponds, not to 3-methyl-4-(4-pyridinyl)-N,N-dimethylbenzeneamine, which would result if the reaction followed the same course as the reaction using N,N-dimethylbenzeneamine, but rather to a compound of unknown composition having the empirical formula $C_{21}H_{21}N_2OCl$.

British Patent 518,886 discloses 2-methyl-4-(4-pyridinyl)benzeneamine, useful as an intermediate for the preparation of dyestuffs, and Forsythe et al., J. Chem. Soc., 2921 (1926) disclose 4-(4-pyridinyl)benzeneamine, for which no utility is given.

SUMMARY OF THE INVENTION

In a composition of matter aspect, this invention relates to certain 3-methyl-4-(4-pyridinyl)benzeneamines, which are useful as cardiotonic agents.

In a further composition aspect, the invention relates to cardiotonic compositions for increasing cardiac contractility and containing, as the active component threof, a cardiotonically effective amount of a said 3-methyl-4-(4-pyridinyl)benzeneamine.

In a method aspect, the invention relates to a method for increasing cardiac contractility in a patient requiring such treatment which comprises administering to such patient a medication containing, as the active component, a cardiotonically effective amount of a 3-methyl-4-(4-pyridinyl)benzeneamine.

In a process aspect, the invention relates to a process for preparing a 3-methyl-4-(4-pyridinyl)-N,N-di-lower-alkylbenzeneamine which comprises reacting pyridine, benzoyl chloride and a 3-methyl-N,N-di-lower-alkyl-benzeneamine in the presence of copper powder and decomposing the reaction mixture with alkali.

In a further process aspect, the invention relates to a process for preparing 3-methyl-4-(4-pyridine)benzeneamine which comprises reacting pyridine, benzoyl chloride and a 3-methyl-N,N-di-lower-alkylbenzeneamine in the presence of copper powder, decomposing the reaction mixture with alkali and reacting the resulting 3-methyl-4-(4-pyridinyl)-N,N-di-lower-alkylbenzeneamine with hydrogen bromide in the presence of pyridine.

In a still further process aspect, the invention relates to a process for preparing 3-methyl-4-(4-pyridinyl)-benzeneamine which comprises heating a 3-methyl-4-(4-pyridinyl)-N,N-di-lower-alkylbenzeneamine with hydrogen bromide and pyridine.

DETAILED DESCRIPTION INCLUSIVE OF THE PREFERRED EMBODIMENTS

More specifically this invention relates to 3-methyl-4-(4-pyridinyl)benzeneamines, which are useful as cardiotonic agents, having the formula:

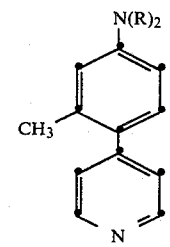

where R is hydrogen or lower-alkyl.

As used herein, the term lower-alkyl means saturated, monovalent, aliphatic radicals, including branched chain radicals of from one to three carbon atoms, and thus represents methyl, ethyl, propyl and isopropyl.

The compounds of formula I where R is lower-alkyl are prepared by reacting pyridine, benzoyl chloride and a 3-methyl-N,N-di-lower-alkylbenzeneamine in the presence of copper powder, the molar ratio of pyridine to benzoyl chloride to the benzeneamine derivative to copper powder being 1.5:1.5:1.0:0.03:, and decomposing the reaction mixture with alkali according to the reaction:

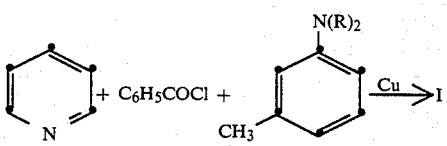

where R is lower-alkyl. The reaction is carried out by heating the reactants on a steam bath, i.e. at a temperature from 90° to 95° C., cooling to ambient temperature, and decomposing the reaction mixture with alkali. Alternatively, the pyridine, benzoyl chloride and copper powder are first heated on a steam bath, then treated with the benzeneamine derivative, followed by further heating on a steam bath, and the mixture decomposed as before with alkali. The course of the reaction can be followed by thin layer chromatography.

These results are quite surprising, in view of the finding by Koenigs el al., Ann. 507, 142-158 (1934) who describe, at pages 147-148 of the reference, a similar reaction between pyridine, benzoyl chloride, N,N-dimethylbenzeneamine (i.e., N,N-dimethylaniline) and copper using the same reaction conditions as described above except that these earlier workers used a molar ratio of pyridine to benzoyl chloride to N,N-dimethylbenzenamine to copper powder of 2.0:1.0:1.0:0.079 to thereby obtain 4-(4-pyridinyl)-N,N-dimethylaniline, analogous to the compounds of the instant invention where R is lower-alkyl. However, as described at pages 150-151 of the Koenigs el al. publication, when reaction was repeated using pyridine, benzoyl chloride, 3-methyl-N,N-dimethylaniline and copper powder and employing precisely the same reaction conditions and molar ratios of reactants as used in the previously described preparation of 4-(4-pyridinyl)-N,N-dimethylaniline, the reaction proceeded by an entirely different course and, instead of producing the expected 3-methyl-4-(4-pyridinyl)-N,N-dimethylaniline, i.e. corresponding to a compound of formula I above where R is methyl, produced instead a compound of unknown composition, having the empirical formula $C_{21}H_{21}N_2OCl$, and presumably corresponding to a 1:1:1 adduct of pyridine, benzoyl chloride and 3-methyl-N,N-dimethylaniline, which was then converted to its "free base". The latter is identified only by its empirical formula, $C_{21}H_{20}N_2O$, and thus corresponds to a compound in which the precursor intermediate product has lost one molecule of hydrogen chloride.

The compound of formula I where R is hydrogen is prepared by heating a corresponding compound where R is lower-alkyl with aqueous hydrogen bromide and pyridine at a temperature from around 200° to 230° C. and isolating the product, in the form of the free base, from an alkaline medium according to the reaction:

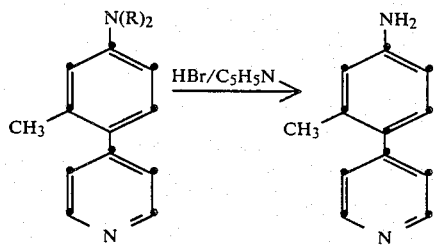

where R is lower-alkyl.

Due to the presence of basic amino groups in the compounds of formula I, i.e. the 4-pyridinyl moiety and the 4-amino or 4-(N,N-di-lower-alkylamino) group, the free base form represented by formula I above reacts with organic and inorganic acids to form acid-addition salts. The acid-addition salt forms are prepared from any organic or inorganic acid. They are obtained in conventional fashion, for instance either by direct mixing of the base with acid or, when this is not appropriate, by dissolving either or both the base and the acid separately in water or an organic solvent and mixing the two solutions, or dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfuric acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid and the like.

All of the acid-addition salts are useful as sources of the free base forms which are generated by reaction of the salts with an inorganic base. It will thus be appreciated that if one or more of the characteristics such as solubility, molecular weight, physical appearance, toxicity, or the like of a given base or acid addition salt thereof render that form unsuitable for the purpose at hand, it can be readily converted to another, more suitable form. For pharmaceutical purposes, acid-addition salts of relatively non-toxic pharmaceutically-acceptable acids, for example hydrochloric acid, lactic acid, tartaric acid, methanesulfonic acid and the like are, of course, employed.

The compounds of formula I, and their acid-addition salts, have been found to be useful as cardiotonics. Their utility as cardiotonics was established by their effectiveness in standard pharmacological test procedures, for example in causing a significant increase in the contractile force of the isolated cat atria and papillary muscle, that is greater than 25% increase in papillary muscle force and right atrial force, while causing only a lower percentage increase in right atrial rate (about one-third or less than the percentage increase in right atrial or papillary muscle force), and also in causing a significant increase in the cardiac contractile force in the anesthetized dog with low or minimal changes in heart rate and blood pressure, that is, an increase of greater than 25% in cardiac contractile force (or cardiac contractility) and less than 25% change in heart rate and blood pressure. The isolated cat atria and papillary muscle procedure and the anesthetized dog procedure are described in detail by Alousi el at., Circ. Research, 45, 666-667 (1979).

The actual determination of the numerical pharmacological data for a particular compound of the invention is readily obtained according to the above-described standard test procedures by technicians versed in pharmacological test procedures without the need for any extensive experimentation.

In clinical practice, the compounds of formula I are normally administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, for example lubricating agents such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents, such compositions can also contain adjuvants, such as wetting and suspending agents, or sweetening, flavoring, perfuming and preserving agents. According to this invention, the compounds for oral administration also include capsules of absorbable material such as gelatin containing the active component either with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. The compositions can also contain adjuvants such as stabilizing, preserving, wetting, emulsifying and dispersing agents.

They can be sterilized, for example by filtration through a bacteria-retaining filter, by incorporation of sterilizing agents in the compositions, by irradiation or by heating. They can also be manufactured in the form of sterile solid compositions, which can be dissolved in sterile water or some other sterile injection medium immediately before use.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus only be determined by the clinician after a consideration of all criteria and utilizing his best judgement on the patient's behalf.

The structures of the compounds of the invention were established by the mode of synthesis, by elementary analyses and by ultraviolet, infrared and nuclear magnetic resonance spectra. The course of reactions was followed, and the homogeneity of the products was ascertained, by thin layer chromatography.

The manner and process of making and using the invention, and the best mode contemplated by the inventors of carrying out the invention, will now be described so as to enable any person skilled in the art to which it pertains to make and use the same. The melting points are uncorrected.

EXAMPLE 1

A mixture of 320 g. (4.05 moles) of pyridine, 560 g. (3.98 moles) of benzoyl chloride, 365 g. (2.7 moles) of 3-methyl-N,N-dimethylbenzeneamine and 5.0 g. (0.079 mole) of copper powder was stirred and heated on a steam bath for ninety-eight hours and then poured slowly with stirring into a solution of 500 ml. of 35% sodium hydroxide and 500 ml. of water. The mixture was stirred for one hour, cooled to ambient temperature and then extracted twice with 1 liter portions of diethyl ether. The combined extracts were concentrated to dryness in vacuo and purified by chromatography on 2.5 kg. of silica gel, eluting first with a 1:1 mixture of hexane: diethyl ether and then with a 2% solution of methanol in diethyl ether to give 65.2 g. of 3-methyl-4-(4-pyridinyl)-N,N-dimethylbenzeneamine, m.p. 106°–109° C.

EXAMPLE 1A

It is contemplated that, by following a procedure similar to that described above in Example 1, substituting for the 3-methyl-N,N-dimethylbenzeneamine used therein a molar equivalent amount of 3-methyl-N,N-diethylbenzeneamine, 3-methyl-N,N-dipropylbenzeneamine, or 3-methyl-N,N-diisopropylbenzeneamine, there can be obtained, respectively, 3-methyl-4-(4-pyridinyl)-N,N-diethylbenzeneamine, 3-methyl-4-(4-pyridinyl)-N,N-dipropylbenzeneamine or 3-methyl-4-(4-pyridinyl)-N,N-diisopropylbenzeneamine.

EXAMPLE 2

To a stirred solution of 48% hydrogen bromide was added, in small portions over about a twenty minute period, 112 g. (0.53 mole) of 3-methyl-4-(4-pyridinyl)-N,N-dimethylbenzeneamine. The mixture was then treated dropwise with 470 ml of pyridine. The resulting solution was then slowly heated to 210°–215° C. while water was allowed to distill off. The resulting melt was heated at 210°–215° C. for ten hours, then cooled and rendered basic by the addition of 35% aqueous sodium hydroxide. The yellow solid which separated was collected, washed with water and dried to give 60.8 g. of crude product which was set aside. The filtrate from the crude product was concentrated to dryness in vacuo, and the residue was dissolved in 600 ml. of water and filtered. The insoluble material was combined with the original first crop to give a total of 67.8 g. of 3-methyl-4-(4-pyridinyl)-benzeneamine, m.p. 121°–124° C.

EXAMPLE 2A

It is contemplated that by following a procedure similar to that described in Example 2 above, substituting for the 3-methyl-4-(4-pyridinyl)-N,N-dimethylbenzeneamine used therein a molar equivalent amount of 3-methyl-4-(4-pyridinyl)-N,N-diethylbenzeneamine, 3-methyl-4-(4-pyridinyl)-N,N-dipropylbenzeneamine or 3-methyl-4-(4-pyridinyl)-N,N-diisopropylbenzeneamine, there can be obtained, in each case, 3-methyl-4-(4-pyridinyl)benzeneamine.

BIOLOGICAL TEST RESULTS

Utility of the compounds of formula I as cardiotonics was established by test results obtained in the isolated cat atria and papillary muscle procedure described above. Data so-obtained expressed in terms of percent change in right atrial rate (RAR), right atrial force (RAF) or papillary muscle force (PMF) at dose levels expressed in terms of micrograms/ml. are given in the table below.

| Dose | RAR | RAF | PMF |
| --- | --- | --- | --- |
| Compound of Example 1 | | | |
| 10 | 22.7 ± 6.7 | 23.7 ± 8.7 | 13.2 ± 11.9 |
| 30 | 48.7 ± 11.5 | 24.7 ± 8.8 | 50.8 ± 10.3 |
| 100 | 33.7 ± 4.5 | 30.0 ± 10.0 | 55.2 ± 18.3 |
| Compound of Example 2 | | | |
| 1 | −2.7 ± 2.7 | 0 ± 0 | 3.0 ± 3.0 |
| 10 | 7.3 ± 1.3 | −14.7 ± 4.1 | 1.6 ± 6.9 |
| 30 | 91.6 ± 29.0 | 29.0 ± 2.6 | 73.0 ± 14.4 |
| 100 | 124.7 ± 32.5 | 117.5 ± 39.6 | 244.2 ± 52.6 |

We claim:

1. The process for preparing a compound having the formula:

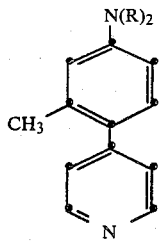

where R is lower-alkyl which comprises reacting pyridine, benzoyl chloride and a 3-methyl-N,N-di-lower-alkylbenzeneamine in the presence of copper powder in a molar ratio of said reactants of 1.5:1.5:1.0:0.03 and decomposing the reaction mixture with alkali.

2. The process for preparing a compound having the formula:

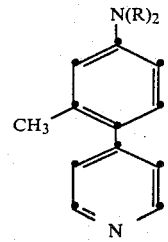

where R is hydrogen which comprises (1) reacting pyridine, benzoyl chloride and a 3-methyl-N,N-di-lower-alkylbenzeneamine in the presence of copper powder in a molar ratio of said reactants of 1.5:1.5:1.0:0.03 and decomposing the reaction mixture with alkali and (2) heating the resulting 3-methyl-4-(4-pyridinyl)-N,N-di-lower-alkylbenzeneamine with hydrogen bromide and pyridine.

3. The process according to claim 1 for preparing 3-methyl-4-(4-pyridinyl)-N,N-dimethylbenzeneamine which comprises reacting pyridine, benzoyl chloride and 3-methyl-N,N-dimethylbenzeneamine in the presence of copper powder.

* * * * *